United States Patent [19]

Futhey et al.

[11] Patent Number: 5,129,718
[45] Date of Patent: * Jul. 14, 1992

[54] MULTI-FOCAL DIFFRACTIVE OPHTHALMIC LENSES

[75] Inventors: John A. Futhey, Petaluma, Calif.; William B. Isaacson, Stanley, N. Dak.; Michael J. Simpson, Maplewood, Minn.

[73] Assignee: Minnesota Mining and Manufacturing Company, Saint Paul, Minn.

[*] Notice: The portion of the term of this patent subsequent to May 26, 2009 has been disclaimed.

[21] Appl. No.: 439,628

[22] Filed: Nov. 21, 1989

Related U.S. Application Data

[63] Continuation-in-part of Ser. No. 176,701, Apr. 1, 1988, abandoned.

[51] Int. Cl.⁵ .......................... G02C 7/04; G02C 7/02; G02B 27/44
[52] U.S. Cl. ........................... 351/161; 351/172; 359/565; 359/570; 359/571; 359/575; 623/6
[58] Field of Search .............. 351/159, 160 R, 160 H, 351/161, 162, 168, 172; 350/162.16, 162.22, 452; 623/6; 359/565, 569, 570, 571, 575

[56] References Cited

U.S. PATENT DOCUMENTS

| | | | |
|---|---|---|---|
| 4,070,105 | 1/1978 | Marzouk | 351/159 |
| 4,146,306 | 3/1979 | Wallach | 350/452 X |
| 4,210,391 | 7/1980 | Cohan | 351/161 |
| 4,338,005 | 7/1982 | Cohan | 351/168 X |
| 4,340,283 | 7/1982 | Cohan | 351/161 |

Primary Examiner—Scott J. Sugarman
Attorney, Agent, or Firm—Gary L. Griswold; Walter N. Kirn; Stephen W. Buckingham

[57] ABSTRACT

An ophthalmic lens exhibiting diffractive power has a plurality of diffractive zones and smooth surfaces. The zones are arranged such that $R_0^2$ does not equal $R_1^2 - R_0^2$ where $R_0$ is the radius of the central zone and $R_1$ is the radius of the first annular zone.

8 Claims, 3 Drawing Sheets

MULTI-FOCAL DIFFRACTIVE OPHTHALMIC LENSES

This is a continuation-in-part application of U.S. application Ser. No. 07/176,701, filed Apr. 1, 1988 now abandoned.

FIELD OF THE INVENTION

The present invention relates to ophthalmic lenses having a plurality of focal lengths.

BACKGROUND OF THE INVENTION

As used herein the term "ophthalmic lens" means vision correction lenses such as contact lenses and intraocular lenses. Other, less common, vision correction lenses such as artificial corneas and intralamellar implants are also included in this definition.

Bifocal spectacle lenses have been known for hundreds of years. In such lenses a first region of the lens is typically provided with a first focal length while a second region of the lens is provided with a second focal length. The user looks through the appropriate portion of the lens for viewing near or far objects.

More recently there has been interest in developing other types of multifocal ophthalmic lenses. Multi-focal contact lenses utilizing an approach similar to that used in spectacle lenses are described in *Contact Lenses: A Textbook for Practitioner and Student*, Second Edition, Volume 2 on pages 571 through 591. Such lenses have serious drawbacks, however, because they require that the lens shift on the eye so that different portions of the lens cover the pupil for distant and close vision. This design cannot be used for intraocular lenses or other implanted lenses, because such lenses cannot shift. Even for contact lenses the design is disadvantageous because it is difficult to insure that the lens will shift properly on the eye for the desired range of vision.

In another design for a bifocal contact lens described in the above-referenced textbook, a central zone of the lens is provided with a first focal length and the region surrounding the central zone is provided with a second focal length. This design eliminates the necessity for shifting the lens by utilizing the phenomenon of simultaneous vision. Simultaneous vision makes use of the fact that the light passing through the central zone will form an image at a first distance from the lens and light passing through the outer zone will form an image at a second distance from the lens. Only one of these image locations will fall on the retina and produce a properly focused image while the other image location will be either in front of or behind the retina. The human eye and brain will, to a great extent, work together to ignore the improperly focused image. Thus the user of such a lens receives the subjective impression of a single well-focused image. A disadvantage of such a lens is that, if the central zone is made large enough to provide sufficient illumination in its associated image in low light situations, i.e. when the patient's pupil is dilated, the central zone will occupy all or most of the pupil area when the pupil contracts in a bright light situation. Thus bifocal operation is lost in bright light. Conversely if the central zone is made small enough to provide bifocal operation in bright light situations, an inadequate amount of the light will be directed to the image associated with the central zone in low light environments. Because the central zone is commonly used to provide distant vision, this can create a dangerous situation when the user of such a lens requires distant vision in low light situations such as when the user must drive a motor vehicle at night.

U.S. Pat. Nos. 4,210,391; 4,340,283; and 4,338,005, all issued to Cohen, teach the use of a plurality of annular regions that direct light to multiple foci and rely upon simultaneous vision to discard unfocused images. They teach the use of alternating concentric Fresnel zones, wherein each of those zones have substantially equal area. The use of such equal area zones causes the lens to provide a diffractive focus of the light. A first focus will occur for the zero order diffracted light while a second focus will occur for the first order diffracted light. Such a structure is known as a diffractive zone plate.

A diffractive zone plate must be designed for light of a particular wavelength and will work most efficiently for light at that wavelength. The radius of the $n^{th}$ zone ($r_n$) in the diffractive zone plates taught in the Cohen patents will be equal to $\sqrt{n}\, r_1$ where $r_1$ is the radius of the central zone. To a reasonable approximation $r_1$ would be equal to $\sqrt{\lambda f}$ where $\lambda$ is the design wavelength and $f$ is the focal length of the diffractive structure. Therefore the $n^{th}$ zone would have a radius equal to $\sqrt{n\lambda f}$.

In designing a diffractive zone plate a design wavelength must be selected. When a desired focal length and wavelength are selected for a lens as taught in the Cohen patents, the area of each of the zones, and thus the location of the boundary of each zone, are determined. This rigid definition of the zones result in a disadvantage to the zone plate structure. In order to obtain an efficient diffractive bifocal operation, a sufficient number of zones must be used. However if the area of the central zone is too large, under bright light situations with the pupil constricted, only a single zone or very few zones will be utilized. Thus the efficiency of the multi-focal operation is greatly reduced.

SUMMARY OF THE INVENTION

The present invention provides a multifocal ophthalmic lens having optical power, at least a portion of the optical power being produced by diffraction. The lens has a plurality of diffractive zones including a circular central zone and a plurality of concentric annular zones. The central zone has a radius $r_0$ and the first annular zone has a radius $r_1$ where $r_1^2 - r_0^2$ is not equal to $r_0^2$. The lens further has two major surfaces, both of which are smooth.

The present invention recognizes that the central zone of an ophthalmic lens utilizing a phase zone plate need not have the same area as the other zones. In one embodiment the central zone is made smaller than the other zones in order to insure adequate multifocal operation. In another embodiment the size and refractive power of the central zone is adjusted to control the distribution of energy between the foci.

DETAILED DESCRIPTION

Figure 1:
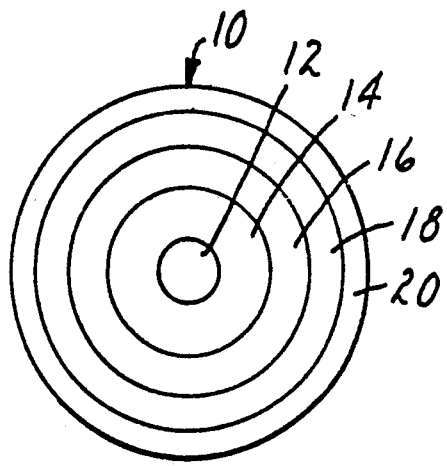
FIG. 1 is a front view of a lens having a flat surface constructed in accordance with the present invention.

An ophthalmic lens, generally designated 10 in FIG. 1, is provided with a diffractive zone plate including zones 12, 14, 16, 18, and 20. Although the drawing shows only five zones, more would typically be provided. The exact number would depend on the amount of change from the base optical power of the lens, the size of the lens and the design wavelength, among other factors. Typical lenses have between 20 and 30 zones. As will be described below the radii of the zones will be affected by several factors including the choice of a design wavelength. In a preferred embodiment the design wavelength is chosen in the spectral region of the greatest photopic sensitivity of the human eye.

The lens of FIG. 1 typically has a base optical power provided by refraction. An additional power is provided by diffraction. Alternatively the entire optical power could be provided by diffraction. The diffractive optical power is provided by separating the zones by optical steps. An optical step causes light rays passing immediately on each side thereof to experience different optical path lengths, where the optical path length is defined in terms of wavelengths of light of a design wavelength. One way of providing optical steps is to provide physical structures on a surface of the lens. Alternatively optical steps may be provided on a smooth surface by varying the index of refraction of the underlying material. Such variation of the index of refraction may be accomplished, for example, by removing portions of the lens material and filling the structures formed thereby with a material having a different index of refraction or by doping portions of the lens with a dopant that causes the index of refraction of the doped regions to change.

The size of the optical steps is defined in terms of optical height. The optical height of a step should be an odd half integral multiple of the wavelength of light of the design wavelength. Typically the optical height is one half wavelength for light of the design wavelength. The term optical height, as used herein, refers to the difference in optical path length in terms of wavelengths of light, for adjacent light rays passing on each side of the step. Thus to provide an optical height of one-half wavelength, the actual height should be $(\lambda/2)/(i_1 - i_2)$ where $\lambda$ is the wavelength of the light in question, $i_1$ is the first index of refraction, typically that of the lens material, and $i_2$ is the second index of refraction, that of the medium bordering the lens or of the modified portion of the lens.

Those skilled in the art of diffractive lenses have generally come to the conclusion that the radii of all zones are uniquely determined when a design wavelength, a focal length, and the indices of refraction are chosen. This conclusion is unduly restrictive.

Figure 2:
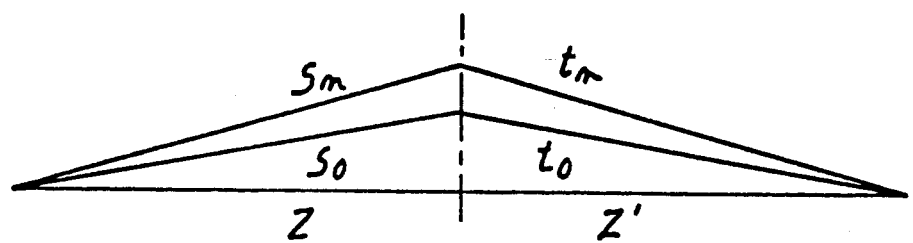
FIG. 2 is a schematic diagram for use in describing the invention.

FIG. 2 will be used to show that more freedom is available in selecting zone radii than taught by the prior art. The example shown in FIG. 2 represents the special case of diffractive zones provided on an otherwise flat surface. In some ophthalmic lenses, such as intraocular lenses, the zones may actually be provided on a flat surface. In others the radius of curvature of the surface is great enough that it may be neglected.

In FIG. 2, z represents the distance from an object to the lens along the optical axis of the lens and z' represents the distance from the lens to the image location along that axis. The distance represented by $s_0$ is the distance from the object to the outer edge of the central zone and that represented by $t_0$ is the distance from the outer edge of the central zone to the image location. Similarly $s_n$ represents the distance from the object to the outer edge of the $n^{th}$ zone and $t_n$ represents the distance from the outer edge of the $n^{th}$ zone to the image. The effect of the unnecessary restriction of the prior art is to require that $s_0$ equal z and $t_0$ equal z'. Instead, as previously explained, the proper requirement is that the optical path length difference from the outer edge of one zone to the outer edge of the next zone must be one wavelength. In order for this condition to be met, the following relationship must hold:

$$s_0\mu_1 + t_0\mu_2 + n\lambda = s_n\mu_1 + t_n\mu_2 \tag{1}$$

where $\mu_1$ is the index of refraction of the medium through which the rays $s_0$ and $s_n$ travel, $\mu_2$ is the index of refraction of the medium through which the rays $t_0$ and $t_n$ travel and $\lambda$ is the design wavelength.

Using the Pythagorean theorem equation (1) may be rewritten as:

$$\sqrt{z^2 + r_0^2}\, \mu_1 + \sqrt{z'^2 + r_0^2}\, \mu_2 + n\lambda = \sqrt{z^2 + r_n^2}\, \mu_1 + \sqrt{z'^2 + r_n^2}\, \mu_2 \tag{2}$$

where $r_0$ is the radius of the central zone and $r_n$ is the radius of the $n^{th}$ zone. Thus the radius of the central zone may be arbitrarily chosen and equation (2) solved to determine the radii of the remaining zones to provide the desired diffractive power. As an approximation, equation (2) may be expressed as:

$$r_n^2 = r_0^2 + 2n\lambda f \tag{3}$$

where f is the focal length of the portion of the optical power of the lens provided by the diffractive structure.

The ability to arbitrarily select the radius of the central zone while providing diffractive optical power can be expressed in terms of the relationships among the radii of the zones. If the radius of the central zone is designated $r_0$, the radius of the innermost annular zone is designated $r_1$ and the radius of the second annular zone is designated $r_2$, the conditions previously described may be expressed by saying that $r_0^2$ is not equal to $r_1^2 - r_0^2$ and $r_2^2 - r_1^2$ is equal to $r_1^2 - r_0^2$. In general, $r_n^2 - r_{n-1}^2$ is equal to $r_{n-1}^2 - r_{n-2}^2$ for values of n greater than or equal to 2.

Since the radius of central zone 12 of FIG. 1 may be chosen arbitrarily, it may be made smaller than the prior art dictates, causing the remaining zones to be moved closer to the center of the lens. Then even when the pupil of the eye is constricted, as in a bright-light situation, a sufficient number of zones will be used to allow multifocal operation of the lens.

If the design wavelength, the focal length and the pupil size of the patient are such that an adequate number of zones can be provided while making the central zone larger than the other zones, such a design is acceptable. If such a design is possible for a particular patient, other advantages may be achieved. For example a zone plate having a different focal length, design wavelength or both could be provided within the central zone. Such an additional zone plate could be used as a method of redistributing the light energy between the foci.

Another advantage of the invention lies in the ability to redistribute the proportion of the light directed to each focus without the use of another diffractive structure in the central zone. By providing a different refractive power in the central zone than that provided in the remainder of the lens, light passing through the central zone can be directed to either of the foci produced by the combined refractive and diffractive power of the remainder of the lens. By adjusting the size of the central zone and the focus to which it directs light, the energy distribution between the foci may be optimized. Thus a patient who must drive a vehicle in low light conditions might require more energy in the far object focus while another patient who does delicate work might require that more energy be provided to the near focus.

Figure 3:
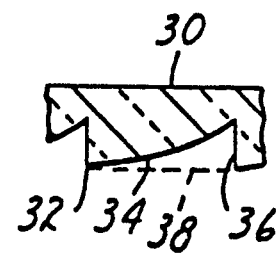
FIG. 3 is a cross-sectional view of a single zone of the lens of FIG. 1.

FIG. 3 shows a cross-sectional view of a single zone of a lens as it would be shaped on the flat surface of the lens of FIG. 1. Those skilled in the art will readily perceive that the vertical scales in FIGS. 3 through 5 and 7 are greatly exaggerated in order to more clearly show the nature of the structures. The anterior side 30 is smooth while the diffractive zones are provided on the posterior side 32. Posterior side 32 includes diffractive zone 34 and step 36. As previously described the optical height of step 36 is $\lambda/2$, where $\lambda$ is the design wavelength. The diffractive zone formed by region 34 and step 36 leaves a cut out section 38 in the posterior side 32 of the lens. As previously described, region 38 may be left open or may be filled with a material having a different index of refraction from that of the lens body.

The shape of the zone surface will affect the diffractive orders to which energy is directed by the structure and the energy distribution among those orders. In a preferred embodiment the shape of region 34 of the illustrated zone is parabolic. The precise shape of the zone is, however, less important to the performance of the lens than the locations of the zone boundaries. The key requirements are that the zone boundaries be properly located and that the zone curves smoothly. Since a spherical zone shape is generally easier to generate than a parabolic one using currently available techniques and a sphere is a reasonably close approximation to a parabola over a small region, a spherical zone shape may be used to approximate the parabola. The spheres that are used in the preferred embodiment are designed in such a manner that the proper step height will be provided between the zones and the center of the spheres lie on the optical axis of the lens. Other shapes may also be used as long as such shapes are a good approximation to a parabola.

Figure 4:
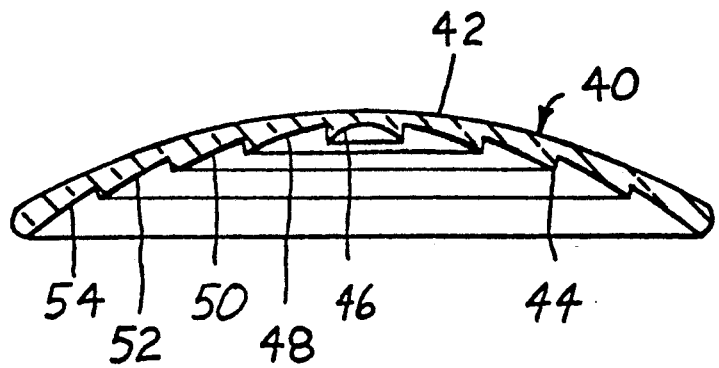
FIG. 4 is a cross-sectional view of a meniscus lens constructed in accordance with the present invention.

FIG. 4 shows a cross-sectional view through the center of a curved lens 40 constructed in accordance with one embodiment of the invention. The lens is a meniscus lens having a smooth anterior side 42 and a diffractive zone plate formed by a structured posterior side 44 having a series of diffractive zones 46, 48, 50, 52 and 54. Alternatively the zones could be formed on the anterior side 40 of the lens, or even on both sides of the lens. As previously described the optical steps separating the diffractive zones such as optical step 56 could also be formed in other ways not requiring an actual physical step.

Figure 5:
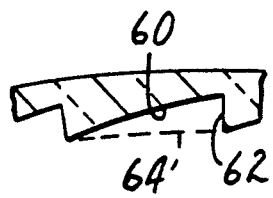
FIG. 5 is a cross-sectional view of a single zone of the lens of FIG. 4.

FIG. 5 illustrates the zone shape for the curved lens 40 of FIG. 4. The zone shown in FIG. 5 has a region 60 and a step 62. The optical height of step 62 is again $\lambda/2$ for the design wavelength. Also shown in FIG. 5 is dashed line 64 that represents the base curve of the lens (i.e. the curve that the lens surface would follow if no diffractive zones were provided). The shape of region 60 is determined in a manner similar to that of region 34 of FIG. 3.

Figure 6:
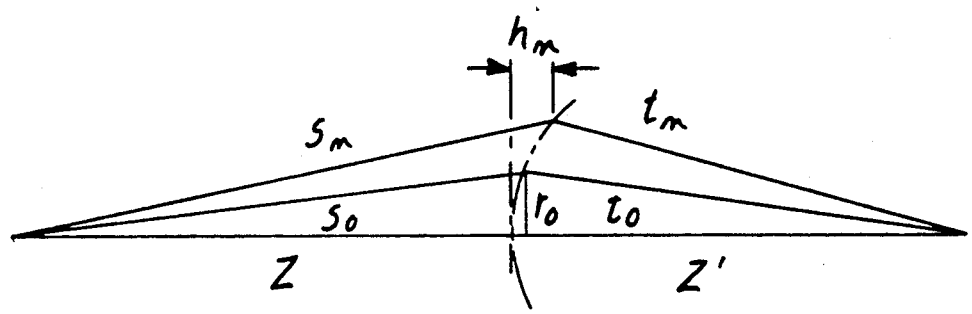
FIG. 6 is a schematic diagram of a lens for use in describing the derivation of the equation for curved surface corrections to zone radii.

When the zones are provided on a curved surface, improved performance may be obtained by introducing a correction for the curvature. The derivation of the curved surface correction will be more readily understood by reference to FIG. 6. A term $\delta$ is introduced representing the difference in optical path length experienced by a light ray traveling from the object to the edge of the central zone to the image location and a light ray traveling along the optical axis. The value of $\delta$ is given by:

$$\delta = s_0\mu_1 + t_0\mu_2 - (z\mu_1 + z'\mu_2) \qquad (4)$$

where $s_0$ is the distance from the object to the edge of the central zone, $t_0$ is the distance from the edge of the central zone to the image location, z is the distance from the object to the lens along the optical axis, $z'$ is the distance from the lens to the image location along the optical axis and $\mu_1$ and $\mu_2$ are the indices of refraction through which the $s_0$ and $t_0$ beams travel, respectively.

The values of z and $z'$ are chosen for the case of an image of an object close to the eye being focused on the retina by the near object focal power of the lens. Typically the physical object is located 30 to 40 cm from the eye. The object distance for these equations, however, is the distance to the image produced by the refractive power of the lens in combination with the cornea. When the object location is on the same side of the lens as the image location, z takes on a negative value. For a contact lens the value of z would typically be about $-32$ mm and the value of $z'$ would be about 30 mm. For an intraocular lens the value of z would typically be about $-20$ mm and the value of $z'$ would be about 19 mm.

As previously described the optical path length difference from the outer edge of a zone to the outer edge of the next zone should be $\lambda$, where $\lambda$ is the design wavelength. From this the optical equation for the $n^{th}$ zone may be written as follows:

$$z\mu_1 + z'\mu_2 + n\lambda + \delta = s_n\mu_1 + t_n\mu_2 \qquad (5)$$

where $s_n$ and $t_n$ are the distances from the object to outer edge of the $n^{th}$ zone and from the outer edge of the $n^{th}$ zone to the image location, respectively. This equation can be rewritten as:

$$z\mu_1 + z'\mu_2 + v\lambda = s_n\mu_1 + t_n\mu_2 \qquad (6)$$

where $$v = n + \delta/\lambda. \qquad (7)$$

From geometric considerations, it may be shown that $$s_n = \sqrt{(z+h_n)^2 + r_n^2} \tag{8}$$

and $$t_n = \sqrt{(z'-h_n)^2 + r_n^2} \tag{9}$$

where $h_n$ is the distance from a plane tangent to the lens on the optic axis to the lens at the outer edge of the $n^{th}$ zone and may be calculated by $$h_n = R_c - \sqrt{(R_c^2 - r_n^2)} \tag{10}$$

where $R_c$ is the radius of curvature of the lens.

Substituting the values from equations 8, 9, and 10 into equation 6 and squaring twice yields:

$$r_n^4(c_2^2-c_3^2)-r^2[2c_1c_2+c_3^2(d^2+d'^2)]+c_1^2-c_3^2d^2d'^2 \tag{11}$$

where
 $d=(z+h_n)$,
 $d'=(z'-h_n)$,
 $c_1=(z\mu_1+z'\mu_2+v\lambda)^2-d^2\mu_1^2+d'^2\mu_2^2$,
 $c_2=\mu_1^2+\mu_2^2$, and
 $c_3=2\mu_1\mu_2$ This equation may be solved by iterative techniques. As previously described the object and image are effectively on the same side of the lens for a typical diffractive structure used in an ophthalmic lens. Therefore $\mu_1$ and $\mu_2$ are equal and the symbol $\mu$ may be substituted for both. Using this substitution and other approximations it can be shown that the following equation provides a reasonable approximation to equation 11:

$$r_n = (v\lambda f/\mu)^{1/2}\frac{1}{2} - f^{3/2}(v\lambda/\mu)^{3/2}\left(\frac{1}{2R_c}\left(\frac{1}{z'^2}-\frac{1}{z^2}\right)-\frac{1}{4}\left(\frac{1}{z^3}+\frac{1}{z'^3}\right)\right) \tag{12}$$

where f is the focal length of the diffractive power of the lens. As an alternative approximation the zone radii may be calculated by solving the following equation for $r_n$:

$$r_n^2 = r_0^2 + 2n\lambda f/\mu - k^2 f^3 (v\lambda/\mu)^2$$

where $$k = \frac{1}{2R_c}\left(\frac{1}{z'^2}-\frac{1}{z^2}\right)-\frac{1}{4}\left(\frac{1}{z^3}+\frac{1}{z'^3}\right)$$

Figure 7:
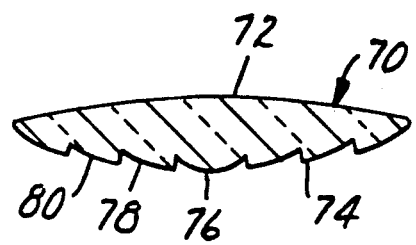
FIG. 7 is a cross-sectional view of a biconvex lens constructed in accordance with the present invention.

FIG. 7 is a cross-sectional view of a biconvex lens, designated generally as 70 utilizing the invention. A lens of the form of lens 70 could be used as an intraocular lens. Lens 70 has a first side 72 and a second side 74. Diffractive zones, such as central zone 76 and annular zones 78 and 80 are provided on side 74. As in the lenses of FIGS. 1 through 6 the radius of central zone 76 may be chosen arbitrarily in order to provide the best functionality for a particular patient. If side 74 is the anterior side of the lens, equation (11) or equation (12) may be used directly to calculate zone radii with correction for the radius of curvature of the surface. If side 74 is the posterior side, those equations may be used by regarding the radius of curvature of the surface as negative.

Figure 8:
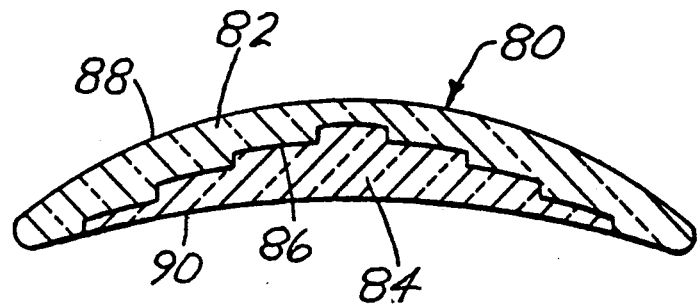
FIG. 8 is a schematic cross section of a meniscus lens according to the invention, having smooth surfaces.

FIG. 8 illustrates a meniscus lens according to the invention having both major outer surfaces smooth. Lens 80 includes a region 82 and a region 84 having differing indices of refraction. The refractive power is provided by diffractive zones such as diffractive zone 86 formed at the interface between regions 82 and 84. This allows major surfaces 88 and 90 to be smooth. The differing indices of refraction could be provided in a number of ways. For example, region 82 or region 84, or both could be doped with a material that alters the index of refraction of the underlying material. In such a structure the base material of both region 82 and 84 could be the same with different types or quantities of dopant. Alternatively regions 82 and 84 could be made of different materials bonded together by any of a number of known techniques such as ultrasonic welding. The key element to the embodiment of FIG. 8 is simply that the diffractive zones are formed on the interior of the lens at the interface between two regions having differing indices of refraction.

In the embodiment of FIG. 8 region 84 would have a lower index of refraction than region 82. Those skilled in the art will readily perceive that region 82 could have a lower index of refraction than region 84. In order to construct such a lens the direction of the curves that form the surfaces of the diffractive zones would be reversed.

The lens of FIG. 8 could be, for example, a contact lens. Such a lens would provide an advantage because a smooth surface would ride on the cornea. This would help to reduce corneal abrasion caused by the sharp corners of the diffractive zones. The lens of FIG. 8 could also be a meniscus lens to be used as an intraocular lens. Some authorities believe that tissue growth over a structured surface on an implanted lens would be greater than over a smooth surface. The structure of the lens of FIG. 8 would help eliminate this problem if in fact it exists.

Figure 9:
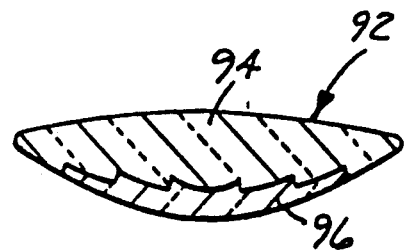
FIG. 9 is a schematic cross section of a biconvex lens according to the invention, having smooth surfaces.

FIG. 9 shows a biconvex lens 92 having a region 94 with a first index of refraction and a region 96 having a second index of refraction, where the first and the second indices of refraction are different. Again the diffractive power arises from the diffractive zones formed at the interface between the two regions having differing indices of refraction. The differing indices of refraction are provided similarly to those of the embodiment of FIG. 8.

The key aspect of the embodiments of FIGS. 8 and 9, beyond those taught with respect to the other embodiments is that a lens according to each of these embodiments has two major surfaces, both of which are smooth.

We claim:

1. A multifocal opthalmic lens having diffractive power, said lens having first and second major surfaces, said diffractive power being provided by a central diffractive zone and a plurality of concentric annular diffractive zones surrounding said central zone, said central zone having a radius designed $R_0$ and each of said annular zones having a radius designated $R_n$ where n is the number of the annular zone counted outwardly from the center zone with $R_1$ being the innermost annular zone and $R_0^2$ is not equal to $R_1^2-R_0^2$ and said first and second major surfaces are smooth.

2. The lens of claim 1 wherein $R_0^2$ is less than $R_1^2-R_0^2$.

3. The lens of claim 1 wherein said lens comprises two material shaving differing indices of refraction having an interface therebetween and said diffractive zones are formed at said interface.

4. The lens of claim 3 wherein $R_0^2$ is less than $R_1^2-R_0^2$.

5. The lens of claim 1 wherein said diffractive zones are formed by introducing a dopant into portions of said lens.

6. The lens of claim 5 wherein $R_0^2$ is less than $R_1^2-R_0^2$.

7. The lens of claim 1 wherein said lens is a contact lens.

8. The lens of claim 1 wherein said lens is an intraocular lens.

* * * * *

UNITED STATES PATENT AND TRADEMARK OFFICE
CERTIFICATE OF CORRECTION

PATENT NO. : 5,129,718
DATED : Jul. 14, 1992
INVENTOR(S) : Futhey et al.

It is certified that error appears in the above-indentified patent and that said Letters Patent is hereby corrected as shown below:

Col. 6, line 27, Replace "$\delta = s_0\mu_1 + t_0\mu_2 - (z\mu_1 + z'\mu_2)$" with -- $\delta = s_0\mu_1 + t_0\mu_2 - (z\mu_1 + z'\mu_2)$ --

Col. 7, line 25, Replace "$^2=$" with --$^2=0$--

Col. 9, line 6, Replace "material shaving" with --materials having--

Signed and Sealed this

Third Day of January, 1995

Attest:

BRUCE LEHMAN

Attesting Officer  Commissioner of Patents and Trademarks